(12) United States Patent
Griffin

(10) Patent No.: US 9,618,700 B1
(45) Date of Patent: Apr. 11, 2017

(54) ORTHOGONAL OUTPUT OPTICAL FIBER

(71) Applicant: InnovaQuartz LLC, Phoenix, AZ (US)

(72) Inventor: Stephen E. Griffin, Peoria, AZ (US)

(73) Assignee: InnovaQuartz LLC, Phoenix, AZ (US)

( * ) Notice: Subject to any disclaimer, the term of this patent is extended or adjusted under 35 U.S.C. 154(b) by 0 days.

(21) Appl. No.: 14/958,057

(22) Filed: Dec. 3, 2015

(51) Int. Cl.
*G02B 6/32* (2006.01)

(52) U.S. Cl.
CPC .................... *G02B 6/32* (2013.01)

(58) Field of Classification Search
CPC . A61B 18/24; A61B 18/22; A61B 2018/2272; A61B 2018/2288; G02B 6/262; G02B 6/32; G02B 6/4296
See application file for complete search history.

(56) References Cited

U.S. PATENT DOCUMENTS

| | | |
|---|---|---|
| 4,669,467 A | 6/1987 | Willett et al. |
| 4,672,961 A | 6/1987 | Davies |
| 4,718,417 A | 1/1988 | Kittrell et al. |
| 4,732,448 A | 3/1988 | Goldenberg |
| 4,740,047 A | 4/1988 | Abe et al. |
| 4,842,390 A | 6/1989 | Sottini et al. |
| 4,967,745 A | 11/1990 | Hayes et al. |
| 5,019,075 A | 5/1991 | Spears et al. |
| 5,061,265 A | 10/1991 | Abela et al. |
| 5,074,632 A | 12/1991 | Potter |
| 5,093,877 A | 3/1992 | Aita et al. |
| 5,104,392 A | 4/1992 | Kittrell et al. |
| 5,106,387 A | 4/1992 | Kittrell et al. |
| 5,125,404 A | 6/1992 | Kittrell et al. |
| 5,192,278 A | 3/1993 | Hayes et al. |
| 5,199,431 A | 4/1993 | Kittrell et al. |
| 5,231,684 A | 7/1993 | Narciso et al. |
| 5,242,438 A | 9/1993 | Saadatmanesh et al. |
| 5,269,777 A | 12/1993 | Doiron et al. |
| 5,290,275 A | 3/1994 | Kittrell et al. |
| 5,292,320 A | 3/1994 | Brown et al. |
| 5,342,355 A | 8/1994 | Long |
| 5,343,543 A | 8/1994 | Novak et al. |
| 5,354,294 A | 10/1994 | Chou |
| 5,428,699 A | 6/1995 | Pon |
| 5,437,660 A | 8/1995 | Johnson et al. |
| 5,468,239 A | 11/1995 | Tanner et al. |
| 5,486,171 A | 1/1996 | Chou |
| 5,495,541 A | 2/1996 | Murray et al. |
| 5,496,307 A | 3/1996 | Daikuzono |
| 5,496,308 A | 3/1996 | Brown et al. |
| 5,498,260 A | 3/1996 | Rink et al. |
| 5,509,917 A | 4/1996 | Cecchetti et al. |
| 5,512,078 A | 4/1996 | Griffin |

(Continued)

*Primary Examiner* — Thomas A Hollweg
*Assistant Examiner* — Mary A El Shammaa
(74) *Attorney, Agent, or Firm* — Synthesis Intellectual Property LLC

(57) ABSTRACT

Herein is disclosed an optical device for orthogonal redirection of electromagnetic radiation. The optical device includes, in one instance, an optical redirection element that includes a lens and an total-internal-reflectance (TIR) bevel, the lens having a principal axis and a lens radius; an optical fiber having a longitudinal axis and having an output surface positioned proximal to the lens, the output surface having an output surface diameter that is less than or equal to the lens radius; where the output surface is eccentric to the principal axis.

19 Claims, 9 Drawing Sheets

(56) References Cited

U.S. PATENT DOCUMENTS

| | | |
|---|---|---|
| 5,530,780 A | 6/1996 | Ohsawa |
| 5,537,499 A | 7/1996 | Brekke |
| 5,562,657 A | 10/1996 | Griffin |
| 5,571,099 A | 11/1996 | Purcell et al. |
| 5,695,583 A | 12/1997 | Bergh et al. |
| 5,737,472 A | 4/1998 | Bernasson et al. |
| 5,807,390 A | 9/1998 | Fuller et al. |
| 5,824,005 A | 10/1998 | Motamedi et al. |
| 5,908,415 A | 6/1999 | Sinofsky |
| 6,102,905 A | 8/2000 | Baxter et al. |
| 6,113,589 A | 9/2000 | Levy et al. |
| 6,246,817 B1 | 6/2001 | Griffin |
| 6,270,492 B1 | 8/2001 | Sinofsky |
| 6,284,085 B1 | 9/2001 | Gwo |
| 6,398,777 B1 | 6/2002 | Navarro et al. |
| 6,398,778 B1 | 6/2002 | Gu et al. |
| 6,522,806 B1 | 2/2003 | James et al. |
| 6,687,436 B2 | 2/2004 | Griffin |
| 6,712,526 B1 | 3/2004 | Fleenor |
| 6,829,411 B2 | 12/2004 | Easley |
| 6,893,432 B2 | 5/2005 | Intintoli et al. |
| 6,986,764 B2 | 1/2006 | Davenport et al. |
| 7,270,656 B2 | 9/2007 | Gowda et al. |
| 7,273,478 B2 | 9/2007 | Appling et al. |
| 7,386,203 B2 | 6/2008 | Maitland et al. |
| 7,463,801 B2 | 12/2008 | Brekke et al. |
| 7,524,316 B2 | 4/2009 | Hennings et al. |
| 7,909,817 B2 | 3/2011 | Griffin et al. |
| 8,073,297 B2 | 12/2011 | Griffin |
| 8,211,095 B2 | 7/2012 | Gowda et al. |
| 8,257,347 B2 | 9/2012 | Neuberger |
| 8,285,097 B2 | 10/2012 | Griffin |
| 8,425,500 B2 | 4/2013 | Hanley et al. |
| 8,435,235 B2 | 5/2013 | Stevens et al. |
| 8,851,080 B2 | 10/2014 | Gowda et al. |
| 2005/0015123 A1 | 1/2005 | Paithankar |
| 2005/0165279 A1 | 7/2005 | Adler et al. |
| 2006/0291061 A1 | 12/2006 | Iyama et al. |
| 2007/0106286 A1 | 5/2007 | Harschack et al. |
| 2008/0287936 A1 | 11/2008 | Stinson et al. |
| 2009/0240242 A1 | 9/2009 | Neuberger |
| 2010/0135617 A1 | 6/2010 | Novak et al. |
| 2010/0179525 A1 | 7/2010 | Neuberger |
| 2011/0038580 A1 | 2/2011 | Griffin |
| 2011/0149589 A1* | 6/2011 | Ko .................. A61B 18/22 362/553 |
| 2011/0282330 A1 | 11/2011 | Harschack et al. |
| 2014/0074072 A1 | 3/2014 | Griffin et al. |
| 2015/0057648 A1 | 2/2015 | Swift et al. |
| 2015/0272679 A1* | 10/2015 | Wang ................. A61B 5/0075 606/15 |

* cited by examiner

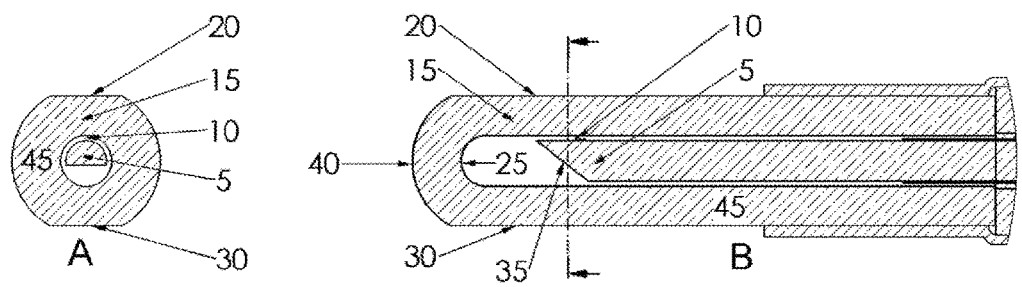
FIG. 1 (Prior Art, Abe)
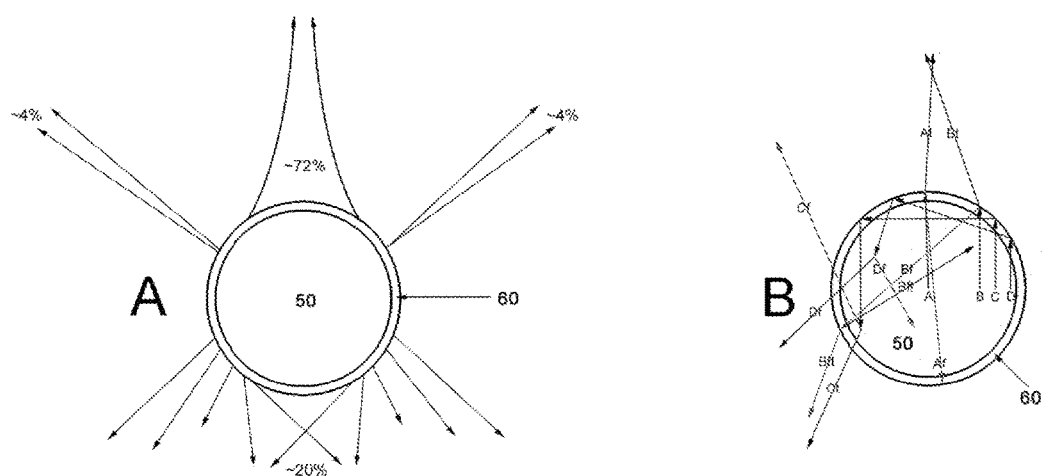
FIG. 2 (Prior Art, Abe)

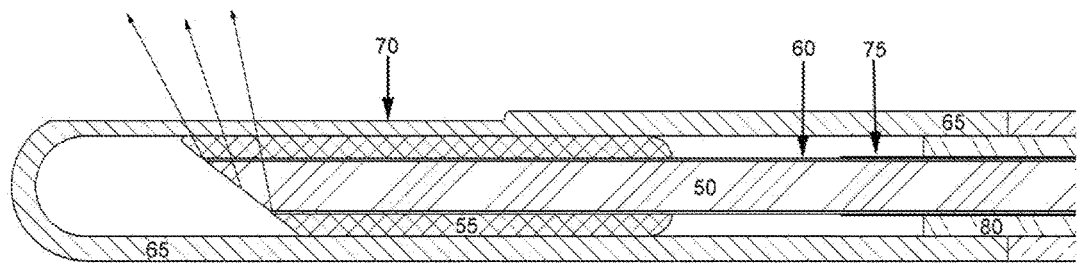
FIG. 3 (Prior Art, Griffin '657)
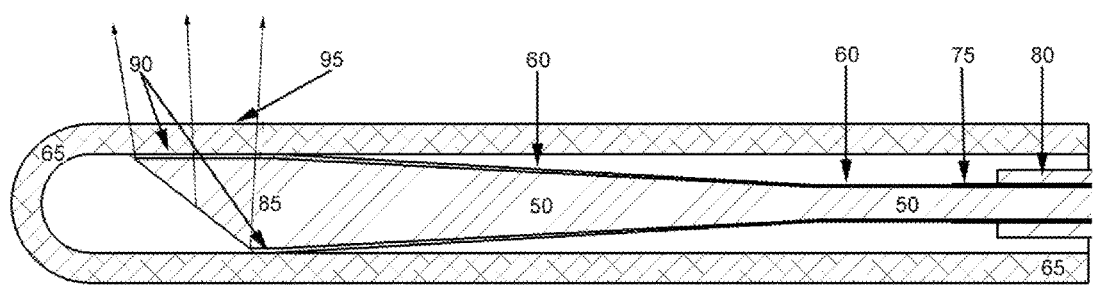
FIG. 4 (Prior Art, Griffin '436)
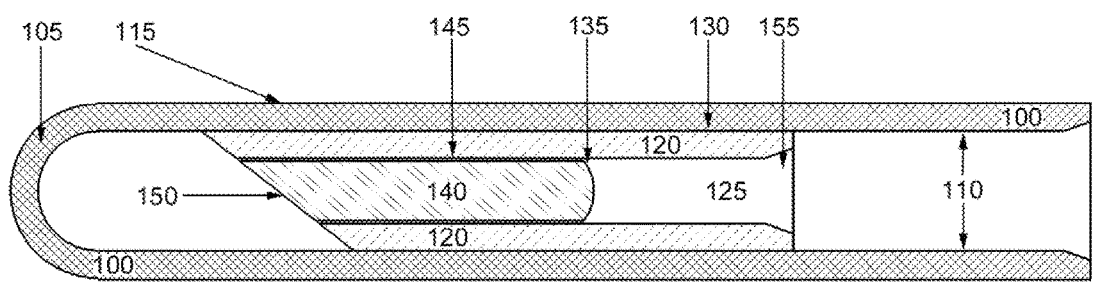
FIG. 5 (Prior Art, Griffin '297)

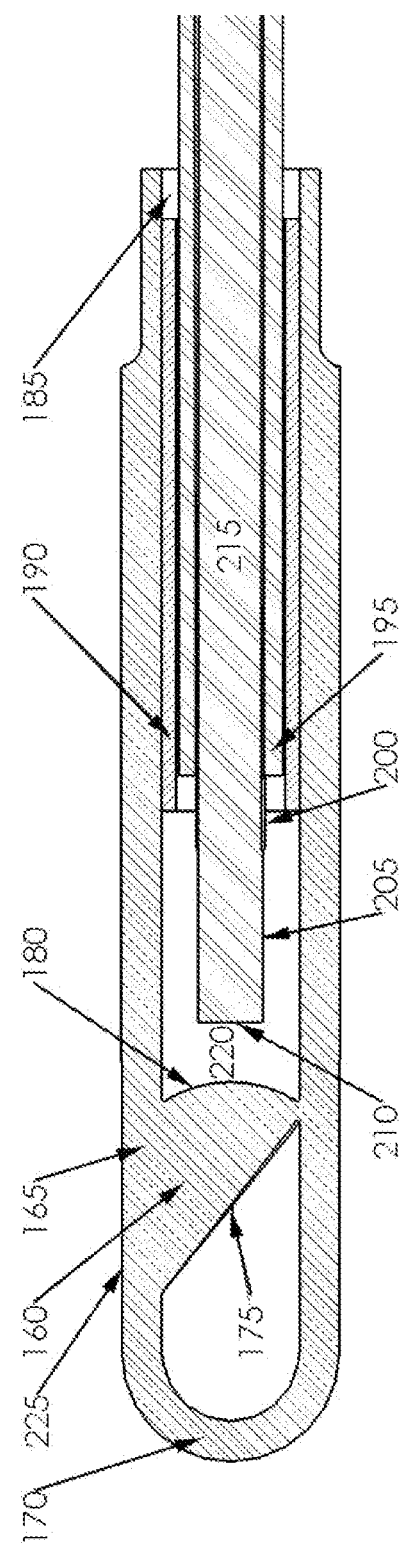
FIG. 6 (Prior Art, Griffin '739)

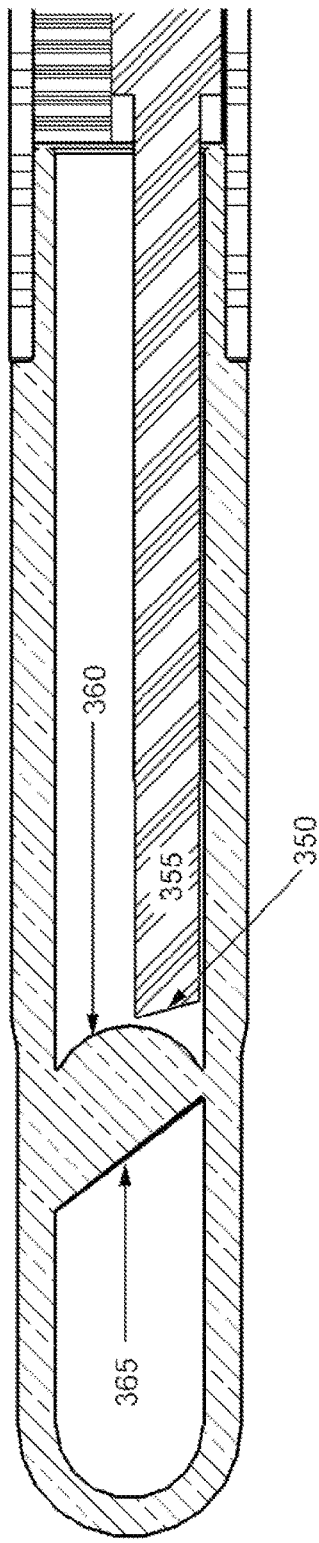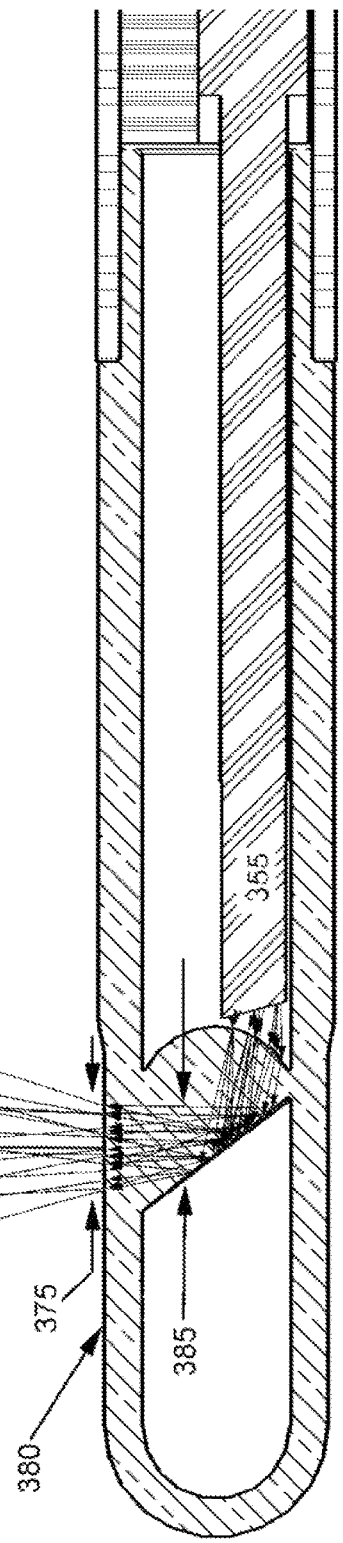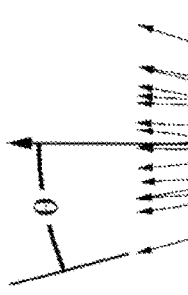
FIG. 9

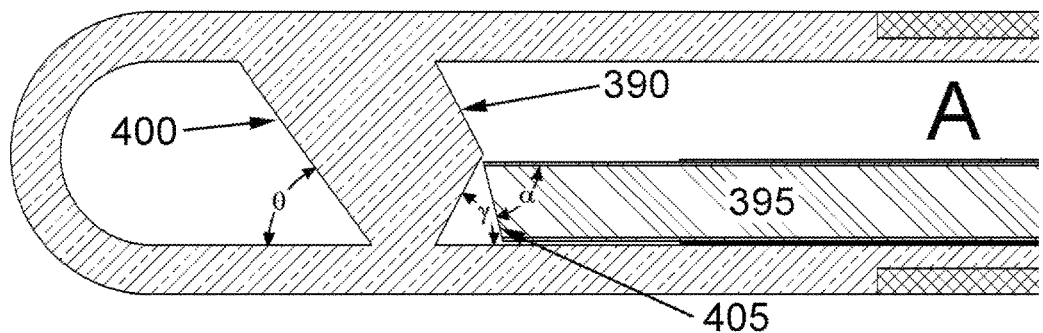
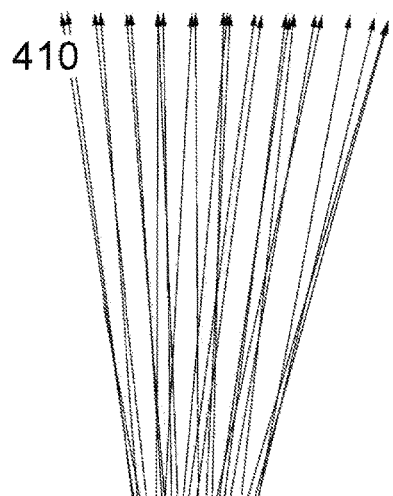
FIG. 10
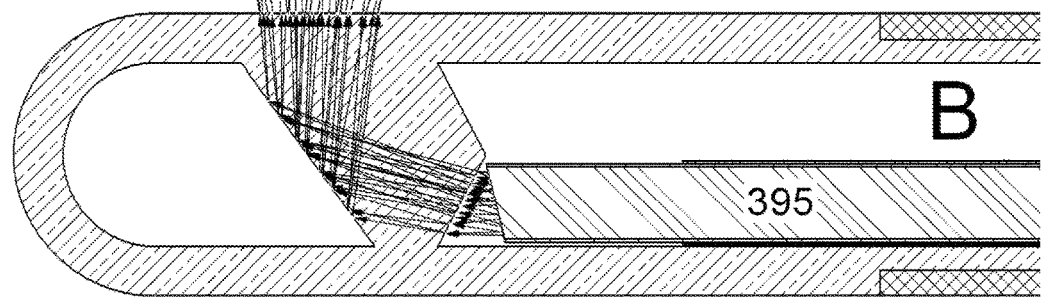

ORTHOGONAL OUTPUT OPTICAL FIBER

FIELD OF THE INVENTION

The disclosure is directed to the objects for, objects that orthogonally (90°) redirect electromagnetic radiation, and the means for and the process of orthogonal redirection of electromagnetic radiation.

BACKGROUND

Electromagnetic energy, such as laser light, is used to perform various surgical procedures including the vaporization of hyperplastic prostate tissues, for example. One optical device that is used with other surgical tools to perform such medical procedures is a side fire optical fiber device, also known as a lateral delivery device.

Lateral delivery optical fiber devices are typically used to redirect delivered electromagnetic radiation in direction other than the fiber longitudinal axis: typically at an angle of 70-90 degrees off the axis. Conventional side fire optical devices operate between angles of approximately 70-80 degrees off axis, or more precisely, 74 to 76 degrees, by reflecting the electromagnetic radiation off of a beveled and optically flat and smooth surface that is machined and polished directly upon the transmitting optical fiber conduit, exploiting total reflection at or below the critical angle as described by Snell's Law. The refractive index conditions for total reflection are typically maintained by protecting the fiber bevel surface with a circumferential protective cap, typically made of fused quartz or fused silica. The redirected output laser light is transmitted through the outer diameter of the fiber itself and then through the cap wall to exit a transmitting surface on the protective cap to address the surgical site.

The maximum off-axis output angle of a conventional side fire fiber is a function of the fiber numerical aperture (NA) which, in turn, is selected for compatibility with the light source focal condition and wavelength, where the wavelength also affects the fiber NA. Lower NA fiber permits higher the off axis redirection angles without axial leakage, at least theoretically, and produces lower the divergence in the laterally redirected energy. Competing designs considerations exist for low NA fiber, e.g. very low NA (0.1) all silica fiber, also known as "ASF" or "silica-silica" fiber, is more sensitive to optical losses under stress than moderate NA fibers, e.g. 0.22 NA ASF, particularly in compression and bending, and producing the lower angle laser foci required to couple to low NA fiber typically increases the laser focus minimum spot diameter which, in turn, requires larger less flexible fiber.

Side fire fibers have been used in some spectroscopic and specialized laser ordinance ignition applications, e.g. laser-induced breakdown spectroscopy, but by far the most common applications of such devices is in surgery, where safety and efficacy considerations have supremacy. Many applications of side fire fibers favor smaller core fibers for the very attributes of optical fiber: flexibility in delivery of concentrated electromagnetic energy. Fiber raw material pricing scales exponentially with diameter, but the minimum fiber diameter that is practical for most surgical applications of side fire fibers is also a function of the laser's focal spot diameter and drift, which is a function of the laser wavelength, $M^2$ beam quality and laser output stability. Some fiber stiffness may be desirable in some applications for compliant torque transfer and resistance to buckling in controlling the fiber positional and rotational orientation. The largest fused silica fibers with any real utility in surgery are approximately 1 mm in diameter. For the most commonly used, 0.22 NA fibers, this diameter includes the fluorine-doped silica cladding but not the polymer coatings; at this time, the most commercially successful side fire fiber for prostate (BPH) surgery has a 0.75 mm core while competing BPH fibers are 0.6 mm core and 0.55 mm core.

Another design consideration for side fire fibers is the maximum off-axis angle that the light may be reflected for a particular fiber choice. Higher angles produce rounder spots (up to 90 degrees with respect to the fiber longitudinal axis), with higher energy density at the transmitting surface, generally, and typically less scattering of the redirecting light. Using Snell's law to calculate the critical angle for a ray that is parallel to the fiber longitudinal axis (at 587.6 nm, for reference, where the refractive indices for fused silica and air are 1.4585 and 1.0003, respectively) yields 43.3 degrees. In the convention of the art, the angle of the polished fiber surface is defined as the complementary angle to the critical angle for convenience of a direct relation to the fiber longitudinal axis, or in this case, 46.7 degrees off-axis. Producing such a polished surface on any fiber would offset the ray that is parallel to the fiber axis by 93.4 degrees—or 3.4 degrees beyond orthogonal—implying that a 90 degree side fire fiber is simple to produce; this result is illusive.

Some light within an optical fiber may be propagated parallel to the fiber axis—light referred to as the "0th order mode" when it is also on the axis—but these rays are not representative of light within the fiber, if they exist at all. Surgical lasers generally couple to fibers by way of a single lens, focusing a much larger beam (e.g. 5 mm) onto the smaller fiber. In determining the focal length of the fiber coupling lens, laser designers usually anticipate the lowest possible NA fiber that will find utility in combination with the laser to select a lens where the highest focal angle is less than the maximum acceptance angle for the fiber—how much less depends upon the designer and the assumptions used—with the goal of insuring the fiber acceptance cone cannot be overfilled. Where the laser designer considers minimum NA for the safety, the fiber designer must consider the maximum NA in side fire fiber design, even where the laser focus condition theoretically under fills the fiber NA. Fiber bending stresses between the laser and the side fire tip may convert lower angle light (or lower order modes) to higher angles, completely filling the fiber NA at the working tip of the fiber.

For 0.22 NA, barring special order, the maximum NA is 0.24 (0.22±0.02). The maximum angle for light propagated within this fiber is just under 9.6 degrees (arcsin NA divided by the fiber core refractive index), so the maximum angle that the fiber tip may be polished for reflecting all light carried within the fiber, often referred to as "the TIR angle", is the angle complementary to the critical angle for the zeroth order ray (46.7 degrees, from above), minus the maximum propagated angle of 9.6, or just over 37 degrees (at 587.6 nm). This result is remarkably consistent across surgically relevant wavelengths (although some designers apparently assume 0.22 for a maximum NA and some designers appear to establish a nominal TIR angle that is a degree or two below the calculated maximum to account for manufacturing variability, etc.) yielding the oft cited range of lateral outputs of 70-80 degrees with respect to the fiber axis.

It bears noting that the maximum divergence of a conventional side firing fiber (akin to that depicted in FIG. 1) is not defined the same way as it is in an axial delivery fiber (through the fiber NA and the refractive index of the working medium) because side fire divergence is also a function of the fiber cladding to core diameter ratio (CCDR), the dimensions of the protective capsule (also known simply as "the cap"), the lateral output angle, the fiber position within the cap, cap geometry and other variables. The output spot of conventional side fire fibers is fundamentally elliptical—albeit an ellipse that is so highly distorted as to be unrecognizable—due to the cylindrical curvatures of the fiber outer diameter, the curvature of the cap wall through which lateral emission passes and the non-orthogonality of the output; fast and slow axes of divergence emerge and correspond to the major and minor diameters of the generally elliptical output spot.

No standards exist for characterizing side fire fiber performance. While most manufacturers do roughly specify the output angle for their fibers, they remain silent on the efficiency of turning the light in the desired direction. Additional parameters such as the irradiance ($W/m^2$) of the spot and radiant intensity (W/sr) of the beam—with efficiency, critical parameters that describe the performance of side fire fibers in all conceivable applications—neither prior art disclosures nor company marketing materials for side fire fibers describe divergence, efficiency or the output beam profile (with American Medical Systems' MoXy™ fiber a notable exception).

Atypical lateral delivery fibers operate at 80-90 degrees, and beyond, by utilizing on-fiber numerical aperture (NA) reduction strategies and/or reflectors less influenced by incident angles, e.g. metals mirrors. The former strategy reduces divergence, increasing radiant intensity, while the latter strategy tends to extend the optical path traversed by the diverging light, reducing irradiance at the target.

A design strategy that increases both irradiance and radiant intensity is described as "fused output" fibers, where the output surface of TIR bevel-tipped fibers is joined to the inner surface of the output cap, eliminating the higher intensity reflections and refractive distortion caused by these highly curved surfaces. During surgery, however, the lateral redirecting tips of fibers are subjected to cycles of rapid heating and cooling as well as sustained and extreme heating. Thermal cycling can exacerbate stresses that are captured within fiber tips and induce fracturing about those stress concentrations, particularly in fused output fiber caps that harbor greater stress from manufacturing, i.e. the external cap cannot been annealed following highly localized melt processing, as is the case in U.S. Pat. No. 5,537,499 (Brekke), U.S. Pat. No. 5,562,657 (Griffin), U.S. Pat. No. 6,687,436 (Griffin), U.S. Pat. No. 8,073,297 (Griffin) and U.S. Pat. No. 7,463,801 (Brekke and Brucker). Transient and sustained high temperatures, at or about the transmitting surface of the cap, also accelerate the endothermic absorption of alkali metal ions within the amorphous silica matrix that forms most caps, lowering the glass viscosity sufficiently to permit rearrangement of the glassy state into thermodynamically favored crystalline states; side fire caps are susceptible to devitrification.

Metallic reflector fibers such as described in U.S. Pat. No. 5,437,660 (Johnson, et al.) may be configured to emit orthogonal radiation, but the reflectors become contaminated with tissue fragments and rapidly degrade. Fiber bevel surfaces coated with metals and multilayer dielectric coatings have been proposed for augmenting or replacing the total internal reflection (TIR) function of the bevel tip, theoretically enabling orthogonal output, e.g. U.S. Pat. No. 8,425,500 (Hanley, et al.), but such coatings have proven difficult to apply uniformly enough to survive the intense laser irradiation used in surgery.

Thermal expansion induced stresses in the side fire optical devices often result in the cap cracking or shattering. Highly localized and intense devitrification causes perforations through protective cap walls with the consequent loss of the refractive index conditions required for total internal reflection. Thermally mediated failure modes are particularly problematic where newer surgical lasers are utilized. Modern lasers produce significantly higher average powers than those of just a decade past, e.g. 120 W holmium laser energy (2080 nm to 2140 nm), 180 W "Greenlight" laser energy (532 nm), up to 250 W diode laser energy (800 nm to 1500 nm), 200 W thulium (2000 nm), and are particularly problematic when side fire fiber devices directly contact tissues during surgery.

Lateral delivery optical fibers for surgery have been described and produced for decades. Early lateral delivery fibers (FIG. 1) were simple in construction: an optical fiber 5 polished at an off-axis angle 35, between 35 and 40 degrees, about which a closed end 40 transparent tube 45, akin to a tiny test tube, is affixed (the tube is often referred to as a "protective capsule" or simply "cap", and the surface through which the light exits is referred to as the "transmissive surface"). Deficiencies with this simple design were quickly recognized and strategies were proposed for mitigation of at least some of the recognized deficiencies; in implementation, most such strategies had little success.

The example in FIG. 1 illustrates an embodiment (U.S. Pat. No. 4,740,047, Abe, et al.) where the original cylindrically curved transmissive surface of the cap, and the cap surface 180 degrees opposing the transmissive surface, are modified to planar surfaces and coated with anti-reflection 20 and reflection coatings 30, respectively. Abe also teaches a third coating 25, a reflector for blocking axial emission, even while teaching away from a 45 degree TIR bevel, which itself is the principal source of such axial emission.

It is apparent that Abe did not fully comprehend the sources of the undesirable emissions that he sought to eliminate, particularly the axial emission due to exceeding the critical angle (for the higher angle modes in the fiber) in using a 45 degree bevel angle. In teaching away from 45 degrees, in favor of 35 degrees to 40 degrees, Abe rationale is for improved visualization of the projected beam and better scope deflection control rather than elimination of axial leakage. If functioning perfectly, the anti-reflection coating 20 Abe proposed to deposit upon the transmissive surface of the cap has very little effect on the rearward reflections (20% portion in FIG. 2A) in that the bulk of these reflections are produced (as depicted in FIG. 2B and in order of contribution to the total): (a) substantially total reflections of extremely acute angles of incidence to the fiber cladding 60 outer diameter curvature, for rays such as D (a skew ray) and C (a meridional ray) at the periphery of the fiber core 50, as taught in U.S. Pat. No. 5,428,699 (Pon), (b) FIG. 1 Fresnel reflections from light transitioning from the fiber 5 into the air gap 10 and from the air gap 10 into the protective cap wall 15 and lastly (c) the Fresnel reflections from the light transitioning from the cap wall 15 into the saline-filled working environment that Abe attempts to mitigate with the antireflective coating 20. Approximately 28% of the light exiting fibers such as taught by Abe (less the antireflective coatings) exits in directions that are surgically useless, contributing to the heating of the fiber tip and may damage non-target tissues during surgery; Abe's anti-reflection coatings reduce these reflections by less than 4%, at best (assuming operation in air).

Although the invention taught by Abe may have been sufficient to avoid damaging non-targeted tissues at the time, owing to the relatively lower laser powers used, the reflective coating 30 taught by Abe for the opposite surface of the cap has minimal effect in preventing such damage owing to the relatively narrow and central portion of the widely spread reverse output that is addressed by the coating (FIG. 2A). As illustrated in FIG. 2B, some rays of light imparting the curved side of an optical fiber, after reflecting from the bevel surface, next encounter cladding:air boundary angles at or near the critical angle for total reflection as defined by Snell's Law, e.g. rays C and D, such that a significant portion of the energy does not exit the fiber in the desired direction, but undergoes complex reflections within the tip instead, eventually exiting in a variety of directions (represented by Ct and Dt) substantially opposite of the desired direction. Low mode angle rays such as A and B with higher incident angles at the cladding:air interface refract in the general direction that is desired (At and Bt), but as the incident angles become lower B, the portion of the energy reflected increases as the portion refracted (exiting) decreases. Partial reflections Bf may be split again, with some of the energy refracting out of the fiber Bft while some is again reflected Bff back into the fiber. In short, the optical model of a standard side fire fiber tip is extremely complex and gives rise to the highly distorted emission that is a well-known characteristic of such devices.

Additional refractions and reflections occur at the air 10 to cap glass 15 interface in FIG. 1 and more refractions and reflections occur at the transmissive surface of the device, although the latter are muted due to the closer match in refractive indices between glass and irrigation fluid in surgery. Minor contributions to the overall scattering (output in directions other than the intended output) result from Fresnel reflections at the fiber core to cladding interface and additional distortion of the output results from the non-orthogonal, off axis angle of emission. In total roughly 28% (the sum of 4%+4%+20%, FIG. 2A) of the energy imparting the fiber bevel exits at angles that are not only surgically useless but actually harm the fiber and may damage non-targeted tissues. Rather than a round spot that diverges symmetrically, the classical side fire fiber output spot is typically reminiscent of a crab with a generally ovoid center (crab body) and radiating streaks (legs) where divergence is highly asymmetric and unpredictable.

Pon describes a more elegant partial solution to the problem of unwanted reflections within the standard side fire fiber output; Pon increases the cladding thickness of the fiber to reduce the amount of light imparting the fiber cylindrical wall at angles acute enough for total reflection. An embodiment of the fiber device described in Pon (Laserscope's ADD-Stat for pre-1999 lasers and Model 2090 for the GreenLight™ lasers that followed) was highly successful in the marketplace with over one million units sold in spite of expense of a disposable device based upon very expensive 1.4 CCDR (Cladding to Core Diameter Ratio) fiber: US$750 each.

Roughly contemporaneous with Pon, two patents (Brekke '499 and Griffin '657, FIG. 3) taught another strategy for reducing unwanted reflections in side firing fibers: fusion of surfaces within the optical output path. In eliminating large differences in refractive indices within the output path, the unwanted critical angle reflections (referred to as "Snell reflections" hereafter, to distinguish them from Fresnel reflections) are essentially eliminated, as are the larger Fresnel reflections and much of the cylindrical distortion of the output. Essentially no back reflections exist for the inventions as described and the output profiles are essentially oval with the relatively the relatively sharp edges typical of standard, axial fiber output profiles. Both inventions describe embodiments that may be produced with far lower cost fiber optic materials than required by Pon (e.g. 1.1 CCDR and 1.05 CCDR fiber) but both inventions also suffer a common flaw: extremely high residual stresses due to the inhomogeneous heating required to achieve fusion without damaging the polymer cladding 75 (also known as "secondary cladding") and the fiber buffer 80 (also known as the fiber "jacket").

As taught by Griffin '657, the fiber core 50 and cladding 60 (analogous to the core and cladding depicted in FIG. 2) is 'overclad' for a short segment near a terminus with a hollow cylinder of fused silica 55, the cylinder inner diameter being fused to the fiber cladding 60 outer diameter. A TIR bevel is formed at 38 degrees relative to the fiber longitudinal axis and the beveled terminus of the fiber is then fused within a closed hollow cylinder of fused silica or protective capsule 65, akin to a test tube, upon the outer diameter of the overcladding sleeve. Finally, like a portion of the art described by Abe, the cylindrical outer diameter of the protective capsule 65 is equipped with a flat 70 to serve as the transmitting surface. This construct harbors high residual stresses that are 'frozen' within the assembly and cannot be removed by annealing for the same reason the fusion heat was applied locally to the regions of fusion; fiber secondary cladding 75 and buffer 80 are heat labile polymers.

The inability to relieve stresses imparted to the fiber termination due to significant and localized differences in thermal history is not the sole problem with on-fiber fusion designs. Defect-free fusions are best carried out slowly such that organic contaminants harbored in the interstices have time to combust and escape before fusion initiates; rapid fusion traps gas bubbles and fusion voids as well as carbonized material. While fused quartz and fused silica have low thermal conductivity, the components are also very small, being limited in diameter and length by the endoscopic working channels (also known as the "forceps channel") through which the devices must pass, e.g. a 6 French forceps channel is typical for flexible ureteroscopes. Heat applied for fusion is quickly conducted to the portion of the protective capsule adjacent to, and/or surrounding, the thermally labile materials.

As such, the heat for fusion is typically applied with a $CO_2$ laser and must be completed in seconds. For example, the rounded terminus (at right, or proximal) of the overclad sleeve 55 is separated by approximately 2 mm from the secondary cladding 75 and approximately 3 mm from the ETFE buffer 80, materials which are also housed within the inner diameter of the protective capsule 65 (in this case having an outer diameter of 1.75 mm and an inner diameter of 1.2 mm.

It is advantageous for surgical performance to produce lateral output fibers that produce undistorted output spot profiles with clearly defined edges and minimal divergence. U.S. Pat. No. 6,687,436 (Griffin) is another fused side fire fiber design, similar to Griffin '657, where the output of the fiber is essentially orthogonal to the fiber longitudinal axis, afforded by reducing the maximum angular mode guided within the fiber by way of tapering the fiber to a larger diameter over a fixed length that is just proximal to the beveled tip. Output at or near 90 degrees is desirable for minimal elliptical distortion in the output spot with higher and more uniform energy density distribution within the spot: an advantage all applications, including ordinance ignition and spectroscopy.

FIG. 4 depicts Griffin '436, an orthogonal output side fire device produced from standard 0.22 NA fiber, with a protective cap 65 about a core 50, cladding 60, secondary cladding 75 and buffer 80 that are analogous to those depicted in FIG. 3. The fiber is up-tapered 85 at one end to approximately 3-fold the original fiber diameter with the goal of reducing the highest angle light energy within the fiber from approximately 8.5 degrees (@0.22 NA) to approximately 3 degrees. The distal tip about the bevel is fused 90 within the cap 65, putting the center of the output (small head arrows) at approximately 88 degrees relative to the fiber longitudinal axis with approximately $\frac{1}{3}^{rd}$ the divergence of the device depicted in FIG. 3 (small head arrows).

The device disclosed in Griffin '436 has the same problems with residual stresses as other fused output type devices, and it shares problems with Brekke '499: the fusion portion 90 ends with an extremely acute angle about the tapered fiber 85 (Brekke is a spot fusion directly between the fiber cladding at the bevel and the protective cap so the acute angle surrounds the Brekke fusion) and the initially optically flat bevel face becomes distorted with the application of the heat for fusion. Such acute angles concentrate stresses and are commonly the originating points for fractures. A further problem in surgical applications of the device depicted in FIG. 4 is that the taper is necessarily made short in order to fit within the dimensional constraints for passing a flexible ureteroscope forceps channel such that the conversion of higher order modes to lower order modes is incomplete (required for efficient redirection of the energy at the TIR bevel), resulting in some axial leakage of energy that exceeds the maximum angle of incidence for total internal reflection.

The stresses harbored within un-annealed fused fiber designs were problematic at average power settings for surgical lasers in use for prostate vaporization a decade ago, where repeatedly and rapidly heating and cooling the side firing fiber caps amplified preexisting stresses and/or flaws, often causing fractures at the junctions of fused and un-fused portions of the assemblies. Modern surgical lasers can deliver more than twice the average power of the former installed base, making the control of Snell and Fresnel reflections even more important and rendering inviable the solutions taught in '499, '657, '436 and even '699.

The device disclosed in Griffin '297, FIG. 5, is a side fire optical device for laterally redirecting electromagnetic radiation-comprising: a cap member 100 comprising a closed end section 105, a tube section having a bore 110, and a transmitting surface 115; a sleeve 120 received within the bore of the tube section, the sleeve including a bore 125 and an exterior surface 130 that is fused to a surface of the bore 110 of the cap member 100; and a fiber optic segment comprising a core 140 and an exterior surface of fluorine-doped cladding 145, the cladding fused to a surface of the bore 125 of the sleeve 120, a beveled end surface 150 formed upon the fused fiber optic and sleeve segment and positioned adjacent the transmitting surface 115 of the cap member 100 and a (chamfered) fiber conduit receiving end 155 opposite the beveled end surface 150 that is within the bore of the outer tube section 110, wherein the beveled end surface 150 is angled relative to a longitudinal axis of the fiber optic segment 140/145 such that electromagnetic radiation propagating along the longitudinal axis of the fiber optic segment 140/145 is reflected by the beveled end surface 150 at an angle that is transverse to the longitudinal axis and through the transmitting surface 115 of the cap member 110 and variations thereof. A convex lens surface 135 may or may not be formed upon the fiber optic segment 140/145.

This invention solves the problem of post-fusion annealing in that the fused side firing mechanism is accomplished entirely within a separate glass structure that may be annealed prior to coupling to the transmitting optical fiber conduit, while also essentially eliminating Snell reflections and greatly reducing Fresnel reflections. Minor Fresnel reflections remain due to the lower refractive index of the fiber optic segment cladding 120 relative to the fiber optic segment core 140 and the sleeve 130 and at the fused surfaces (due to contamination, captured gases, differential surface chemistry, etc.) but close examination of the invention described in '297 reveals numerous shortcomings.

Most of the claimed functions taught in '297 are illusory beyond the physical separation of the cap (and lateral turning elements) from the transmitting optical fiber conduit (thermally labile materials). In brief, the utility of the sleeve 120 that is fused about the fiber optic segment 140/145 is taught to be for aligning the fiber optic conduit (core and cladding within bore 125, secondary cladding and buffer within bore 110) and for displacing the TIR surface 150 from the heat used for fusing the fiber segment 140/145 and sleeve 120 into the cap 100, reducing fusion associated distortion of the TIR surface. A concomitant result of using the sleeve over the fiber is an extension of the optical path, addition of a new fusion surface (where no fusion surface is perfect) and minimization of the optical aperture of the lens 135 produced on the fiber optic segment 140. Adding the sleeve to the design also reduces the thickness of the protective cap 100, rendering the device more fragile and more easily perforated by devitrification.

The use of fiber optic material for the segment 140/145 renders the segment length immaterial, easing assembly, yet also renders the lens 135 without function unless the mated optical fiber conduit is of substantially smaller core than the fiber optic segment 140/145 and the segment itself is shorter than twice the effective focal length of the lens 135, least some of the 'focused' energy leak through the cladding 145. Further, the fluorine dopant in the fiber optic segment 140 cladding may diffuse into the sleeve 120 and cap 100 during annealing, and during surgical heating, predisposing the glass cap to devitrification. Additional deficiencies exist where compared to later designs, such as those taught in U.S. patent application Ser. No. 14/578,739 (Griffin)—filed Dec. 22, 2014, the disclosure of which is incorporated herein in its entirety—and the art taught herein.

It would be useful and novel to provide a means for minimizing potential Fresnel reflections, even those resulting from the relatively similar refractive indices of fiber cladding 145 and fiber core 140 materials at fused surfaces, and for eliminating Snell and Fresnel reflections, within a self-contained lateral output assembly (within which a transmitting optical fiber conduit may be subsequently attached) that enables a truly orthogonal output (relative to the fiber longitudinal axis) with divergence similar to, or lower than, that of the transmitting optical fiber conduit. Griffin '739 teaches remedies for the failings of '297 that meets many of these challenges.

FIG. 6 is a preferred embodiment taught in '739, wherein a quartz or silica rod is rounded to a convex lens 180 on one end and a bevel is machined on the opposite end 175. The shaped rod 160 is fused within a tube of like material 165 that is closed on one end 170, comprising a lateral delivery capsule. The invention becomes a very high efficiency lateral delivery device upon introducing an optical fiber 215 through the open end 185 of the closed tube. The fiber is centered within the lateral delivery capsule via a sleeve 190 about the outer buffer 195. The delivery tip of the fiber 205, comprised of the fiber core 210 and fluorine-doped cladding 205, is denuded of polymer cladding 200 and buffer 195 in the immediate vicinity of the output 210. The opposite end of the fiber 215 (not shown) is connected to a laser source and delivers the laser energy to the lens element 180, where the light is partially collimated or focused before imparting the TIR bevel 175 for redirection off the fiber longitudinal axis.

The embodiment of '739 described above and depicted in FIG. 6, where the lateral delivery capsule outer diameter is 2.2 mm, is compatible with 7 French bore forceps channels within the cystoscopes used for accessing the prostate gland. The optical fiber is a standard 0.22 NA, 1.1 CCDR, 0.6 mm silica core fiber and is centered within the 1.4 mm bore of the lateral delivery capsule and fixed in position with adhesive. Fresnel reflections from the fiber core to the air gap 220 transition are coupled back into the fiber core 210 toward the laser source. The Fresnel reflections from the air 220 to convex lens surface 180 are directed generally toward the open end of the capsule, but in a highly divergent solid cone such that very little of this energy imparts laser labile materials such as the fiber secondary cladding 200, buffer 195 and adhesive. Testing in an aqueous environment produced no thermal damage to the fiber buffer or secondary cladding at 200 watts average power for 15 minutes (980 nm, CW).

Approximately 100% of the energy that enters the shaped rod 160 through the lens 180 is redirected laterally through the transmitting surface 225 of the capsule 165 where the final refractive index transition—capsule to saline irrigation fluid—produces a small Fresnel reflection. Tests of this device under surgical conditions (150 W, CW at 2000 nm in non-contact vaporization of tissue), have failed to expose any propensity for typical side fire fiber failure modes at and beyond 200 kilojoules of total energy applied: in excess of the energy required for many surgical applications. Use for vaporization of tissue in direct contact and above 120 watts average power (2000 nm) does produce devitrification damage but the point at which degradation of performance begins has yet to be determined.

The approximately 75 degree (central) output angle (relative to the fiber longitudinal axis) exhibits perpendicular divergence of approximately 12 degrees and parallel divergence of approximately 6 degrees, in air, as compared to the highest performance side fire fiber currently marketed at 15 degrees and 7 degrees, respectively (MoXy™ specifications per American Medical Systems literature).

U.S. patent application Ser. No. 14/020,289 (Griffin, et al.), filed Sep. 6, 2013 teaches the art enabling the MoXy fiber: a low divergence, high power lateral fiber that utilizes coaxial water cooling. Referring to FIG. 3, MoXy is essentially a hybrid of Griffin '657 and a modified, but relatively conventional side fire fiber. A capsule 65, having a very thin wall, is fused directly about a bevel tipped fiber 50 and sealed like a test tube about the bevel tip to preserve the refractive index needed for total internal reflection; the sleeve 55 is omitted. This delicate side fire fiber is then enclosed within a robust capsule, much as a conventional bevel tipped fiber is enclosed within a conventional side fire fiber capsule 45 as depicted in FIG. 1. Griffin '289 deviates from convention in failing to completely seal the outer capsule at the distal end, leaving a port for communicating fluid from within the capsule to outside of the capsule, at or about the location between the arrows at 25 and 40. The opposing, open end of the outer capsule is affixed to a cannula having a lumen for communicating fluid to the capsule under pressure or gravity flow. The bevel tipped fiber, sealed within the thin wall inner capsule, is centered within the larger, outer protective capsule such that fluid delivered to the capsule (by way of the cannula) forms an annular cooling jacket about the inner capsule and exits the hole in the traditionally sealed capsule at the distal terminus.

By filling the space between the inner capsule and the outer capsule with saline, the Fresnel reflections and the cylindrical distortion plaguing conventional side fire fibers are greatly reduced. Residual stress resulting from fusion of the thin wall inner capsule about the bevel tipped fiber is reduced by using the very thin cylinder and the inner capsule is shielded from thermal cycling by the outer capsule and the continuous coolant fluid flow, greatly reducing the risk of fracture from thermal cycling about internal stresses. The fluid flow also cools the outer protective capsule from within, largely preventing it from rising to temperatures sufficient to initiate tissue adhesion and devitrification. The MoXy fiber operates at 180 W, quasi-CW at 532 nm and performs exceptionally well through 650 KJ of total applied energy.

Side fire fibers that are currently available to surgeons are exclusively single use—they are discarded post-operatively with disposable device costs ranging from approximately $500 (Lumenis DuoTome) to more than US $1000 each (MoXy). High performance fibers like MoXy are competent for completing surgeries on the largest of prostate glands, even in cases where a patient has been taking drugs such as Flomax for years and/or the patient has had a prior treatment by laser (VLAP, PVP, HoLAP), microwave (TUNA) or electrocautery device (TURP). More than one fiber is commonly needed to complete such cases where lesser performance fibers are utilized.

The fiber optic conduit and laser connector represent roughly 80% of the materials costs for producing a classical side fire fiber, and between 50% and 70% of the labor costs are directed toward producing the distal termination (side fire tip), particularly in forming the TIR bevel on the fiber. Although a great deal of the higher cost of the MoXy fiber is due to the use of a larger fiber than is usual (0.75 mm core), much of the cost is also due to the expense of providing the coaxial cooling to the double cap design. It would be useful and novel to provide a side fire fiber capable of being used in multiple surgical sessions through interoperative reprocessing or where the protective cap may be replaced interoperatively (and perhaps even intraoperatively). It would be useful and novel to provide a high performance side fire fiber at far lower cost than MoXy by eliminating the need for coaxial cooling and on-fiber production of TIR bevels.

SUMMARY

A first embodiment is an optical device for orthogonal redirection of electromagnetic radiation that includes an optical redirection element that includes a lens and a total-internal-reflectance (TIR) bevel, the lens having a principal axis and a lens radius; an optical fiber having a longitudinal axis and having an output surface positioned proximal to the lens, the output surface having an output surface diameter that is less than or equal to the lens radius; and wherein the output surface is eccentric to the principal axis.

Another embodiment is a side fire optical device for orthogonal redirection of electromagnetic radiation that includes a lateral delivery cap that includes a longitudinal centerline; and an optical fiber within the lateral delivery cap, the optical fiber having a fiber axis that is parallel to but not centrosymmetric with the lateral delivery cap longitudinal centerline.

Yet another embodiment is a side fire optical device for orthogonal redirection of electromagnetic radiation that includes a tube portion having a one-piece construction consisting of fused quartz and/or fused silica, including a guide section and an open-end section, the open-end section and the guide section divided by a lens, the open-end section including a bore which terminates at the lens, the open-end section shaped to receive a fiber optic cable, the guide section including a light path from the lens to a reflecting surface and then to a transmitting surface, the reflecting surface configured to direct electromagnetic radiation from the lens through the transmitting surface at a side of the tube portion; and a fiber optic conduit asymmetrically positioned within the bore of the open-end section.

BRIEF DESCRIPTION OF THE FIGURES

For a more complete understanding of the disclosure, reference should be made to the following detailed description and accompanying drawing figures wherein:

FIG. 1 is two orthogonal, magnified cross-sections (FIG. 1A and FIG. 1B) illustrating the essential features of prior art (adapted from Abe, et al.).

FIG. 2 is cartoons of magnified fiber cross-sectional cartoons illustrating; FIG. 2A (from Pon) the variety of off-axis angles for misdirected rays in conventional side fire fibers, and the primary (desired) output for side fire fiber optic devices in prior art and FIG. 2B (adapted from Pon) where the sources of some principal misdirected rays are identified.

FIG. 3 is a magnified cross-section view of prior art Griffin '657.

FIG. 4 is a magnified side cross-section view of prior art Griffin '436.

FIG. 5 is a magnified side cross-section view of prior art Griffin '297

FIG. 6 is a magnified side cross-section view of prior art patent application Griffin '739.

FIG. 9 is two identical cross-section views of a preferred embodiment with 9A identifying key physical features and 9B illustrating optical performance features through superimposition of a computed ray trace for the device.

FIG. 10 is two identical cross-section views of a preferred embodiment with 10A identifying key physical features and 10B illustrating optical performance features through superimposition of a computed ray trace for the device.

Figure 7:
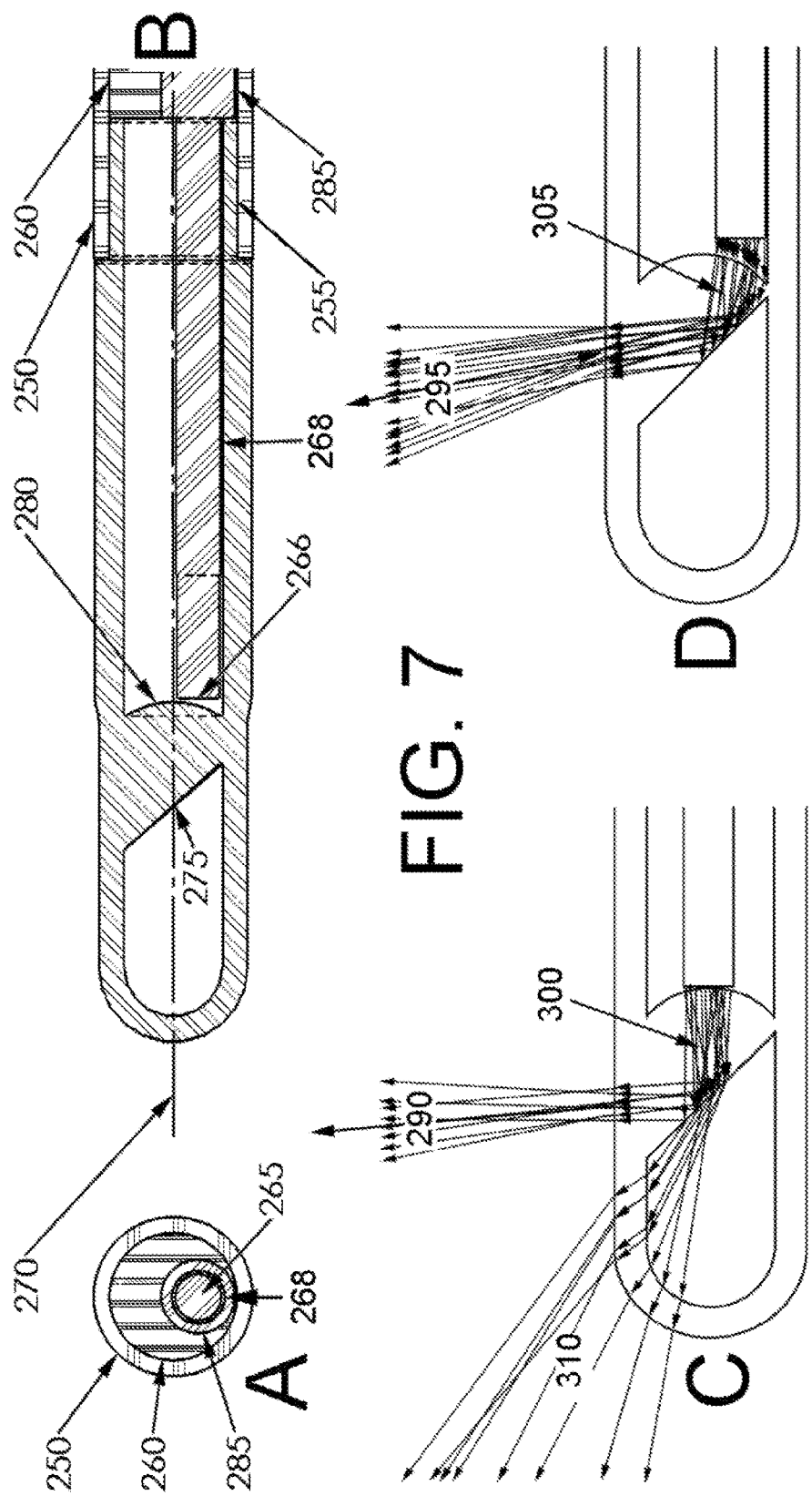
FIG. 7 is four illustrations, two orthogonal and magnified cross-section views (FIG. 7A and FIG. 7B) of an 80 degree side fire fiber and two cartoons FIG. 7A and FIG. 7B illustrating the contribution of a single element of the disclosed art for increasing permissible lateral angles of output.

While specific embodiments are illustrated in the figures, with the understanding that the disclosure is intended to be illustrative, these embodiments are not intended to limit the invention described and illustrated herein.

DETAILED DESCRIPTION

The invention claimed and described herein includes fiber optic assemblies (optical devices) for lateral redirection of laser light (e.g., light for surgery, spectroscopy, or detonation of ordinance). A preferred embodiment utilizes a one-piece side fire cap, for example, as described in U.S. patent application Ser. No. 14/578,739 (Griffin) which is incorporated herein in its entirety. The side fire cap includes an optically polished surface for redirecting electromagnetic energy (a total internal reflectance (TIR) bevel surface) carried upon a short cylinder of uncoated (not clad) and optically transparent material. The opposing end of the cylinder carries a convex or conical lens surface. The capsule is, preferably, made of the same material or similar material as the optical redirection element (e.g., the short, shaped cylinder). The capsule and the optical redirection element are fused to produce a one-piece side fire cap of a single composition, preferably fused quartz or fused silica, or of mixed composition, preferably fused quarts and fused silica. The side fire cap includes a closed end in contact with the TIR surface and including an enclosed space of air, or preferably a partial or high vacuum. The opposing end of the side fire cap (e.g., an open end) includes an open bore which is adapted to receive an optical fiber.

The herein disclosed optical device can further include a transmitting optical fiber. The optical fiber can be, on one end, equipped or adapted for coupling to one or more light sources, a spectrometer, a photo detector, or, preferably, a laser. The optical fiber can further include an output end equipped with a flat, circular or elliptical, output ("the laser fiber output surface"). Herein, the output from the optical fiber is preferably positioned within the open bore of the side fire cap.

As described above, the optical redirection element can include a convex or conical lens. For example, the short cylinder of uncoated optical material can be equipped with a cone in place of the convex lens for coupling the output from the laser fiber to the TIR surface. Furthermore, the optical fiber output may be equipped with a lens, for example an angle polished end or other optical treatment, such as tapers, for coupling to the lateral cap. Lenses within the lateral cap structure may be cylindrical, hemispherical, spherical sections, aspheric, laser best form or meniscus lenses in concave or convex forms.

Some instances of the optical device can include a hollow metallic shroud surrounding the lateral cap, equipped with an output window for the redirected light from the lateral cap, and secured to the optical fiber buffer coating (sometimes called a "jacket") for protection of the lateral cap element. Unlike prior art side fire fibers with the delicate bevel tipped optical fibers, the herein described optical device includes providing a means for replacing caps because the laser fiber tip (flat output surface) is a relatively rugged, flat polished or lens-ended surface. The metallic shroud can provide reversible coupling between a section that is secured about the lateral cap and a section secured to the laser fiber buffer thereby enabling the lateral cap to be replaced easily.

In another instance, the side fire cap may be attached to a semi-rigid tube or cannula, the opposite end of which terminates with a reversible coupling to an extracorporeal control device. In some examples, the cannula and cap are affixed and provide a part which may be removed and replaced in unison.

Preferably, the present invention provides a new and useful method of producing self-contained lateral cap devices for redirecting electromagnetic radiation when attached to laser fibers, at angles that are at least centrally orthogonal to the original axial output. A new and useful construct for redirecting electromagnetic radiation when attached to laser fibers, at angles at least centrally orthogonal to the original axial output and where reflections and distortions of the output are essentially eliminated. A new and useful construct for redirecting electromagnetic radiation when attached to laser fibers where a variety of beam shaping and steering elements may be exploited within the lateral cap design, and for the laser fiber coupling to the lateral cap. A new and useful construct for redirecting electromagnetic radiation when attached to laser fibers where the lateral cap may be replaced during a surgical session and/or between surgical sessions. Still further, the invention itself, both as to its structure and its operation, together with the additional objects and advantages thereof, will best be understood from the following description. It is intended that the inventions not be limited only to the specific structure, material or acts unless so stated, but include any and all structures, materials or acts that perform the claimed function, along with any and all known or later-developed equivalent structures, materials or acts for performing the claimed function.

Notably, the herein described embodiments, preferably, provide an orthogonal output of laser light based on an input along the axis of the optical fiber. Herein, the term "orthogonal" means the laser output has a central output ray that is about 90° from the longitudinal axis of the optical fiber, preferably, within the range of 85° to 95°, 85° to 92°, or 85° to 90°.

Tissues adhere to fiber caps where the temperature of the glass (or sapphire or metal) is high enough to "cook" the tissue (irreversibly denature proteins and drive Maillard reactions) but not high enough to rapidly vaporize the tissue (or burn it to exhaustion) within the fluid irrigated surgical environment. Such conditions are afforded by highly distorted divergent outputs where a continuum of irradiances are present on the cap surface; well defined outputs minimize opportunities for tissue adhesion by compressing the continuum, between very low irradiance to the vaporization threshold irradiance, into compact spaces. Like tissues in a frying pan, tissues that adhere to fiber caps first turn brown and then blacken. Blackening is due to carbon (carbonization) particle formation and growth. Carbon particles absorb and scatter greater and greater amounts of light as they accumulate, and this absorbing surface encroaches closer and closer to the vaporization threshold barrier about the output spot. As absorption locales favoring devitrification and dissolution build upon the transmissive surface, further heating the cap and expanding the surface area favoring tissue adhesion, a positive feedback loop is established. This "tissue adhesion failure cascade" is the foundation of a long-held thesis (Griffin '657) that poor output quality advances fiber failure, particularly in side fire fibers: a thesis that has met with considerable resistance within the field.

A corollary to the tissue adhesion failure cascade thesis is that the area of the transmitting surface through which the lateral output passes is proportional to the susceptibility to tissue adhesion. All other parameters being equal, including radiant intensity, the distribution of irradiance about a larger surface area necessarily increases the area within the irradiance continuum wherein irradiance favors tissue adhesion and carbonization. A true 90 degree output side fire surgical fiber offers advantages in the precision of laser energy application as well meeting the goals stated above; a round output profile that is familiar to the user and uniform in irradiance and divergence and that does not shift in position relative to the fiber tip (as fiber to target tissue separations change) enables far more desirable, predictable and reproducible surgical outcomes.

One embodiment of the herein described optical device is depicted in FIG. 7. Therein, the fiber core 265 is adjacent to or proximal to the inner diameter of the orthogonal delivery cap such that the output of the fiber 266 imparts the lens element 280 below the lens/device centerline 270. Therein, the lens 280 asymmetrically distorts the diverging fiber output such that the most unfavorable mode angles 300 delivered by a center-symmetric fiber cap orientation (addressing the TIR surface at angles larger than the zeroth order mode) are refracted to more favorable angles 305 (addressing the TIR surface at angles smaller than to slightly larger than the zeroth order mode) for interaction with the approximately 42° TIR bevel 275. FIG. 7C provides a computer-generated ray trace for the center-symmetric fiber-cap orientation whereas FIG. 7D provides the ray trace for the eccentric fiber-cap orientation. Notably, moving the fiber off of center eliminates the forward emission 310 (missing rays in output 290), and while the calculated outputs 295 in 7D are not orthogonal, as defined herein, the central output ray is at a higher angle—calculated to be approximately 80 degrees—than is possible within the prior art.

In one instance, the off-of-center positioning of the fiber 265 is accomplished within an eccentric bore cannula 260 housing the buffered 285 fiber 265, which is in turn housed within a second cannula 250 that overlaps a step 255 machined upon the cap outer diameter at the open end. To enable positioning the 0.55 mm core ASF (secondary cladding 268 diameter of 0.63 mm) low enough within the cap it is necessary to exclude the approximately 1 mm diameter buffer 285 from entering the lateral delivery cap.

For example, the optical device depicted in FIG. 7 can include an optical redirection element that includes a lens 280 and a total-internal-reflectance (TIR) bevel 275. The lens 280 having a principal axis aligned with the centerline 270 of the optical device and further having a lens radius. Preferably, the lens diameter is equal to or approximately equal to the inside diameter of the open-end section of the lateral delivery cap. Furthermore, the optical fiber has a longitudinal axis and an output surface 266. Preferably, the output surface 266 is positioned proximal to the lens, for example, within less than 1 mm, 0.5 mm, 0.4 mm, 0.3 mm, 0.2 mm, 0.1 mm, 0.09 mm, 0.08 mm, 0.07 mm, 0.06 mm, or 0.05 mm. Preferably, the optical fiber output surface 266 has an output surface diameter that is less than or equal to the lens radius. Still further, the optical fiber and the lens are oriented, and preferably affixed, in a position where the output surface is eccentric to the principal axis. That is, in one instance, the longitudinal axis of the optical fiber is neither aligned with nor concentric with the lens' principal axis. In a preferably instance, the output surface is external to the principal axis. That is, an outside diameter of the output surface does not overlap with the principal axis and/or the optical device centerline. In another instance the output surface is adjacent to the principal axis; that is, the outside diameter of the output surface is collinear with the principal axis and/or optical device centerline.

As shown in FIG. 7B, the longitudinal axis of the optical fiber can be, and preferably is, parallel to the principal axis.

Therein, the output surface 266 is perpendicular to the longitudinal axis of the optical fiber and adjacent to a convex lens. Notably, the optical device can include a lateral delivery cap that encompasses or includes the optical redirection element. Preferably, the lateral delivery cap is a one-piece construction that includes the optical redirection element. The lateral delivery cap includes an open-end section and the optical fiber is positioned within the open-end section, preferably, adjacent to the inner diameter of the lateral delivery cap. Preferably, the optical device shown in FIG. 7B provides (as shown in FIG. 7D) a central-output angle that is greater than about 80 degrees 295.

Figure 8:
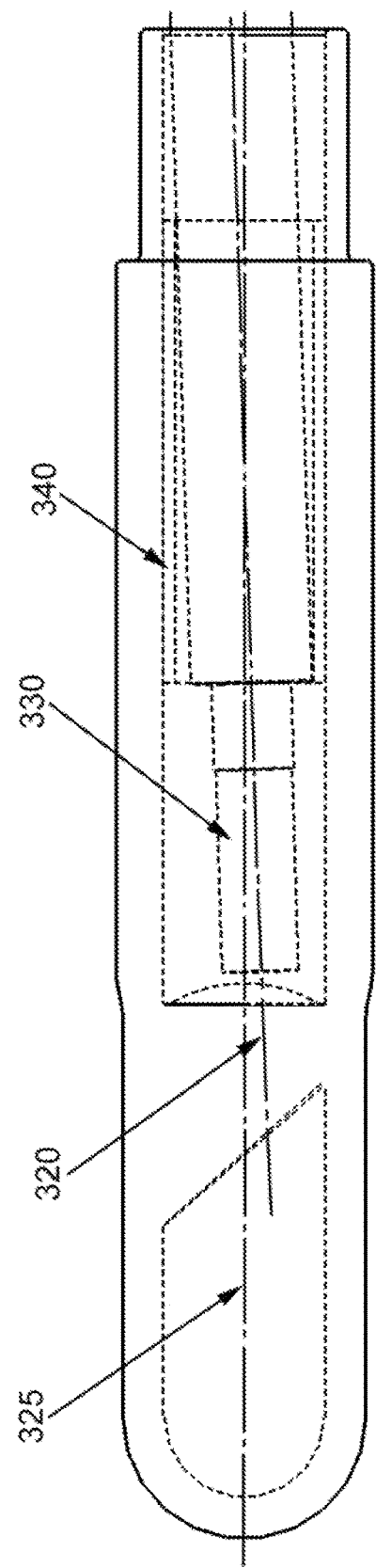
FIG. 8 is a side view of a basic embodiment of the invention.

Another instance, depicted in FIG. 8, includes an optical fiber 330 within a lateral delivery cap, where the optical fiber is canted off of, not parallel to, the centerline 325. Notably, in this instance the lateral delivery cap includes a dimensioned sleeve 340 that was eccentric, canted, or an improper fit (for example, had a bore that was 0.2 mm too large for the fiber). In one example, the fiber 330 became canted within the sleeve 340 and was affixed with longitudinal axis of the optical fiber out of parallel with the centerline (e.g., when installed within the lateral delivery cap, the fiber longitudinal axis 320 was approximately 4 degrees displaced from the lateral delivery cap longitudinal axis 325). The output from the cap can be very similar to that depicted in FIG. 7D, and relative to the fiber longitudinal axis (as opposed to the cap longitudinal axis) the output can be close to orthogonal (for example, having a central output ray at an angle greater than 80°, 85°, or 87°).

FIG. 9A depicts an instance wherein true orthogonal output (90°) can be obtained. Therein, the optical device includes an output surface 350 that has an angular polish. The output surface 350 is preferable planar and angled relative to the longitudinal axis of the optical fiber. Accordingly, the surface is elliptical. Preferably, the output surface 350 is positioned to refract energy exiting the fiber to angles that are stigmatically focused by the lens 360. Therein, the TIR bevel surface 365 may be produced at angles exceeding 38 degrees and even exceeding 45 degrees (relative to the longitudinal axis and/or the lens principal axis) while continuing to reflect 100% of the radiation delivered to the TIR surface 365. As shown in FIG. 9B, the effect of the optical device on light rays emitted from the optical fiber are orthogonally redirected and the overall output from the optical device is centered about the 90 degree central ray 370.

Orthogonal output is achieved with the embodiment depicted in FIG. 9, but the dimensional parameters such as lens curvature, the TIR bevel angle and fiber polish angle must be manufactured accurately and precisely to achieve true orthogonality. These combined factors making the device somewhat challenging to manufacture reproducibly. Myriad combinations of dimensional parameters do work, however, providing a degree of design control over the spot diameter 375 at the transmitting surface 380 and divergence beyond the focal waist 385, e.g. a larger lens curvature requires a lower TIR bevel angle which affords less focusing effect, presenting a larger spot at the transmitting surface 380 but with lower divergence θ. It is relevant to note that the relatively narrow tolerances for the dimensions of the optical elements in the device depicted in FIG. 9 are far less challenging where the delivery fiber is less than completely filled with angular modes; all optical modeling referenced or depicted herein is for 0.22 NA fiber under mode-filled conditions unless otherwise indicated.

In another example, as depicted in FIG. 10, the lens 390 can be a conical solid (or conical lens). As shown in FIG. 10B, the central ray of the output can be in excess of 90° (e.g., at approximately 95° relative to the fiber longitudinal axis) or beyond the orthogonal, and the forward most diverging rays 410 can be only a few degrees short of orthogonal (e.g., about 88° or about 89°). In this example, the extreme off-axis redirection can be accomplished by first steering the output of the optical fiber 395 by polishing the output 405 at an angle α (e.g., about 8° to about 20°, about 12° to about 16°, or about 15°) for refraction then refracting the light again at the cone input surface 390 angle γ (e.g., about 50° to about 70° or about 60°) before imparting the TIR bevel 400 angle θ (polished at the critical angle for total internal reflection, but where the condition for the worst case ray has been greatly altered; for example, about 50° to about 60° or about 55°)

In this instance, a focusing effect provided by a convex lens (e.g., 360 in FIG. 9A) can be lost and, thereby, divergence from an example that incorporates a conical lens can be greater than the respective divergences in an example that incorporates a convex lens. Likewise, all focusing effects are lost in replacing the cone surface 390 with a simple bevel angle (replacing the compound optical element with a simple prism) where normal divergence causes the TIR bevel surface to overfill, resulting in a return of undesirable output angles seen in conventional side fire fibers.

The ratio of the diameter for the delivery fiber and the diameter of the optical element may be increased to compensate for overfilling the TIR bevel in a prism substituted design, but this is contrary to the need in surgical applications, resulting in a more fragile lateral fiber device with a more bulbous protective cap; it is not without functionality, but is readily apparent to be a suboptimal solution. A more attractive embodiment is the lateral fiber device depicted in FIG. 10 where the extreme off-axis redirection is replaced by simple orthogonality, permitting looser manufacturing and tolerances for the optical elements involved while providing new optimum lateral redirection efficiency, irradiance, radiant intensity and output spot symmetry.

Another preferred embodiment is the device as depicted in FIG. 9, where the tip 350 of the delivery fiber 355 is polished flat, orthogonal to the fiber longitudinal axis, and includes a laser launch end of the fiber which is modified to partially collimate the energy carried within the fiber (e.g., as disclosed in U.S. Pat. No. 9,122,009 and U.S. patent application Ser. No. 14/809,871, the disclosures of which are incorporated herein in their entirety; or by other means known in the art, such as down tapered fiber launch (the fiber input aperture is reduced relative to the fiber diameter)). This embodiment is favored for providing higher irradiance at the transmitting surface than the conical variation (FIG. 10A, with flat polished fiber delivery), canted fiber variation (FIG. 8) and prism variant. The conical variation (FIG. 10A, with angle polished or flat polished delivery fiber tip) is favored for manufacturing reproducibility.

That is, one embodiment is an optical device for orthogonal redirection of electromagnetic radiation. The optical device can include an optical redirection element that includes a lens and a total-internal-reflectance (TIR) bevel. The lens has a principal axis and a lens radius. The optical device further includes an optical fiber having a longitudinal axis and having an output surface positioned proximal to the lens. The output surface having an output surface diameter that is less than or equal to the lens radius and wherein the output surface is eccentric to the principal axis. In one instance, the output surface is external to the principal axis. The optical device preferably having the longitudinal axis of the optical fiber parallel to the principal axis.

In one instance of the optical device, the lens is a convex lens. In another instance of the optical device the lens is conical. In either of these instances, the output surface can be perpendicular to the longitudinal axis of the optical fiber or planar and angled relative to the longitudinal axis of the optical fiber. In one example, the output surface is perpendicular to the longitudinal axis of the optical fiber. In another example, the output surface is planar and angled relative to the longitudinal axis of the optical fiber.

The optical device can further include the lateral delivery cap. The lateral delivery cap, preferably, having a one-piece unitary construction (e.g., a single composition having no discernable seams or connections) that includes the optical redirection element. The lateral delivery cap having an open-end section with the optical fiber is positioned within the open-end section, preferably against an internal surface of the open-end section.

Preferably, this optical delivery device provides an orthogonal redirection of laser energy provided through the optical fiber. More preferably, the central-output ray angle (i.e., the degree of orthogonal redirection as measured as a deflection from the longitudinal axis of the optical fiber) is greater than 80°. Even more preferably, the central-output ray angle is in the range of 80° to about 95°, about 85° to about 95°, about 88° to about 92°, or about 90°.

Another embodiment is a side fire optical device for orthogonal redirection of electromagnetic radiation which includes a lateral delivery cap that has a longitudinal centerline (e.g., as provided by the principal axis of the lens). The side fire optical device further including an optical fiber within the lateral delivery cap where the optical fiber has a fiber axis that is parallel to but not centrosymmetric with the lateral delivery cap longitudinal centerline. In one instance, the fiber axis is offset from the lateral delivery cap longitudinal centerline by about 0.5 to about 1.5, about 0.75 to about 1.25, about 0.9 to about 1.2, about 1 to about 1.1 times a cross-sectional radius of the optical fiber. Preferably, the fiber axis is offset from the lateral delivery cap longitudinal centerline by about the cross-sectional radius of the optical fiber, thereby an outside surface of the fiber core is approximately aligned with and parallel to the longitudinal centerline. More preferably, an outside surface of the fiber core is radially displaced from the longitudinal centerline by at least the cross-section radius of the optical fiber.

In one instance, the side fire optical device includes an optical fiber that has an output face which is perpendicular to the fiber axis. In another instance, the side fire optical device includes an optical fiber that has a flat-elliptical output face. Preferably, the elliptical output face is at an angle α to the fiber axis, wherein α is less than 89°, is between 89° and 45°, 89° and 50°, 89° and 55°, 89° and 60°, 89° and 65°, 89° and 70°, 89° and 75°, or 89° and 80°.

Preferably, the lateral deliver cap includes a redirecting element that has a lens and a reflecting surface, preferably a TIR surface. In one example, the lens is centrosymmetric about the lateral delivery cap longitudinal centerline. The lens can be a convex or a conical lens. In one preferable instance, the lens is convex; in another preferable instance the lens is conical. In yet another preferable instance, the lens is convex and the optical fiber has an output face perpendicular to the fiber axis. In still another preferable instance, the lens is convex and the optical fiber has a flat-elliptical output face. In yet still another preferable instance, the lens is conical and the optical fiber has a flat-elliptical output face.

In a most preferable instance, the lateral delivery cap provides (or is adapted to provide) a central ray output angle of greater than 85°, 86°, 87°, 88°, 89°, 90°, 91°, 92°, 93°, 94°, or 95°. The lateral delivery cap, additionally and preferably, provides (or is adapted to provide) a beam divergence maximum of less than 12°, 10°, 8°, 5°, or 3° (in 5% saline).

Yet another embodiment is a side fire optical device for orthogonal redirection of electromagnetic radiation that includes a tube portion having a one-piece construction, and a fiber optic conduit asymmetrically positioned within the bore of the open-end section. The tube portion consisting of fused quartz and/or fused silica, including a guide section and an open-end section, the open-end section and the guide section divided by a lens, the open-end section including a bore which terminates at the lens, the open-end section shaped to receive a fiber optic cable, the guide section including a light path from the lens to a reflecting surface and then to a transmitting surface, the reflecting surface configured to direct electromagnetic radiation from the lens through the transmitting surface at a side of the tube portion.

Figure 11:
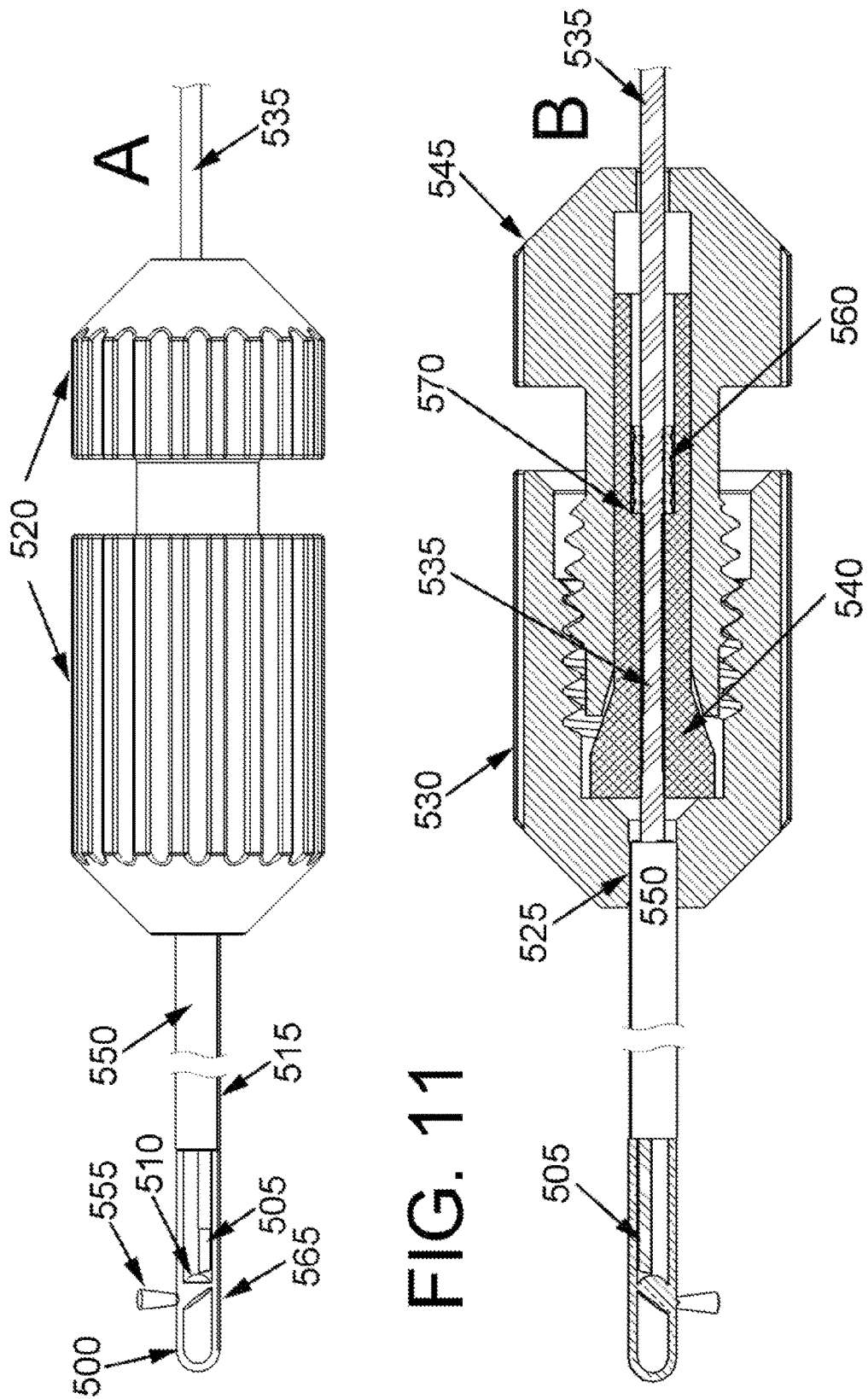
FIG. 11 is two views of a cannula equipped embodiment of the invention where 11A is a side view and 11B is a cross-section.

FIG. 11 depicts an embodiment of the orthogonal output 555 fiber optic device where the one-piece cap 500 for housing a bevel tipped fiber 505 and for refraction of the output (as in the embodiment depicted in FIG. 9), is positioned with the fiber optic output adjacent the input lens surface 510. The cap 500 is carried and affixed within a nested two piece cannula 550 like that described in FIGS. 7 and 9, the inner cannula (not shown) having an eccentric bore for locating the fiber 505 off of, but parallel to, the cap 500 longitudinal axis.

The outer diameter of the cannula 550 is affixed within the collet closer/torque control device 520 within the bore 525 of the distal half 530 of the collet closer. The buffered fiber 535 is immobilized within the collet 540 that closes onto the fiber buffer when the proximal half of the collet closer 545 (or collet holder) it tightened within the distal half 530. A forward travel limiter 560 is affixed to the buffered fiber 535 by crimping or adhesive and stops within the collet 540 at 570 to prevent damage to the fiber during initial assembly and reassembly (for resposable embodiments).

Two aligned orientation marks may be provided: a marking of metals such as gold, platinum or palladium deposited onto the cap 565 via reduction of an organometallic ink for ceramics (e.g. Hanovia Liquid Bright Gold), located 180 degrees opposite the orthogonal output and a marking 515 on the length of the outer cannula 550 produced by etching, scribing or printing on thin-walled metallic cannulae or co-extrusion or printing on polymeric cannulae. Refractory metals as orientation marks resist thermal damage and are appropriate for positions near the lateral output where lower cost markings that extend to the torque control device offer extracorporeal orientation information.

Figure 12:
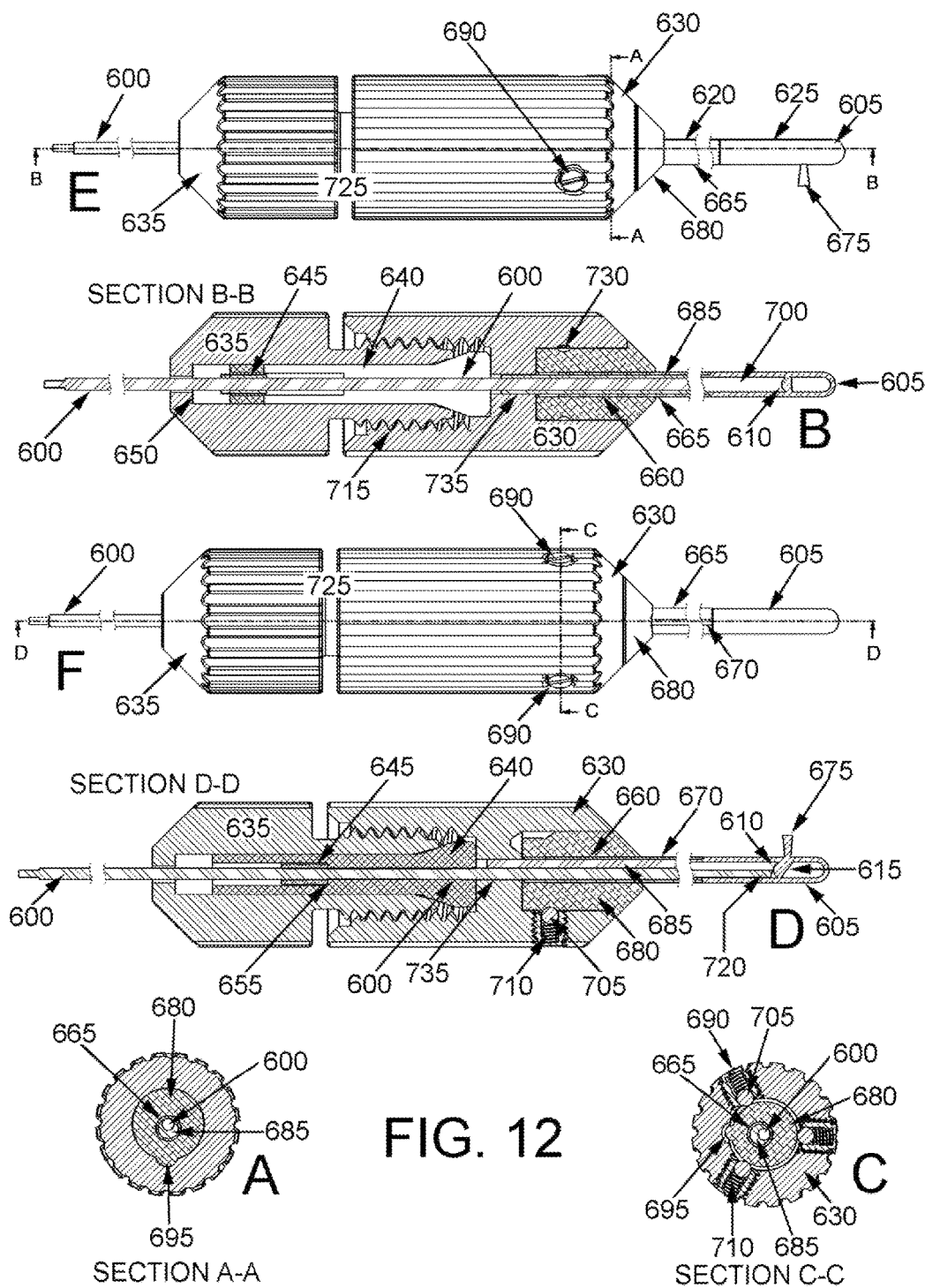
FIG. 12 offers six views of a resposable embodiment of the invention: two orthogonal side views 12E and 12F, two longitudinal cross-sections of the side views 12B and 12D, and two cross-sections 12A and 12B.

A resposable embodiment of the invention is depicted in FIG. 12 where "resposable" means a device, within which a component or components, such as a surgical tip patient contact assembly, is optionally disposable and in which one or more other components, such as a transmitting fiber optic conduit for use with the optionally disposable part, is reusable.

In order to minimize carryover of biological contaminates from patient to patient in reprocessing medical devices, it is preferable that all patient contacting surfaces be replaced in reprocessing: in this case, the fiber cap 605 and the outer cannula 665. A second consideration in reprocessing medical devices is minimization of the risk of damaging the reusable subassembly in cleaning and handling during reprocessing. The output tip 720 of the fiber 600 is the most delicate portion of the side fire fiber devices described herein. A tertiary requirement for reprocessed medical devices is that the reprocessed device functions with equivalent efficacy as the new device. For the devices described herein, efficacy depends upon accurate reproduction of the optical output characteristics which requires the fiber tip 720 to reproducibly find the same location relative to the input surface of the lens 610.

FIG. 12D depicts the fiber device in functional position. A silica core fiber 600 is equipped with an angle polished output 720 that is positioned adjacent to the input surface of the convex lens 610 within the one-piece lateral redirection cap 605 of the orthogonal output device such that refracted light exiting the angled tip fiber 720 is stigmatically focused upon the TIR surface 615 and emitted at approximately 90 degrees with respect to the longitudinal axis of the fiber 600. The fiber 720 position within the cap 605 is maintained adjacent to the cap wall by a cannula 685 having an eccentric lumen ("inner cannula") and the spacing between the fiber tip 720 and the input lens 610 of the cap 605 is maintained by a closed collet 640 within a fiber control device ("torquer" or "torque controller") 725. The forward position of the fiber tip 720 is determined by the forward travel limiter 645, crimped or otherwise adhered to the fiber buffer, stopping within the collet 640 at 655.

FIG. 12B depicts the fiber in a retracted position where the collet 640 has been opened (by loosening the threads 715 that hold the cannula holder 630 and collet holder 635 together) and the fiber has been pulled into the inner cannula 685 approximately 1 centimeter or at least enough for the polished fiber tip 720 to be completely within the eccentric bore of the inner cannula 685, as illustrated by its absence 700. The fiber may be retracted approximately ½ centimeter further if required, at a maximum, where the forward travel limiter 645 stops on the inner surface of the collet holder at 650.

The outer cannula 665 is adhered within a snap-in outer cannula carrier 680 by means of adhesive or other restraining method, within the outer cannula carrier bore 660. The inner cannula is adhered similarly within the cannula holder 630 bore 735. With the fiber 600 released within the collet 640, the snap-in outer cannula carrier 680 may be released such that the used outer cannula 665, cap 605 and outer cannula carrier 680 may slide over the inner cannula 685 until free of the device. A new cap, cannula and snap-in carrier may be slipped over the inner cannula 685. With the key 695 of the snap-in cannula carrier aligned with the keyway in the cannula holder 630, the snap-in cannula carrier may be guided into the cannula holder 630 and pressed into place, retained in position by three spring 710 loaded ball bearings 705 within set screws 690 (set at 120 degree intervals about the cannula holder 630) where the bearings find the locating groove 730. There is no risk of the fiber tip 720 impacting the lens 610 during reassembly due to the retracted state.

To restore function to the device, the fiber 600 may be pressed forward until the forward travel limiter 645 stops within the collet 640. Closing the collet secured the fiber position for surgical use. The position of the fiber tip 720 within the cap 605 and the position of the corresponding orientation mark 625 on the cap and outer cannula 620 are assured at the time of manufacturing, requiring no alignment by reprocessing technicians. (A third orientation mark 670 is depicted in FIG. 12F where the fiber output 675 would be toward the reader. This mark is on the outer cannula only and is of a universal warning color such as bright red, indicating the fiber will fire at the viewer if energized.)

Although the present invention has been described with reference to preferred embodiments, workers skilled in the art will recognize that changes may be made in form and detail without departing from the spirit and scope of the invention.

What is claimed:

1. An optical device for orthogonal redirection of electromagnetic radiation, comprising:
   an optical redirection element that includes a lens and an total-internal-reflectance (TIR) bevel, the lens having a principal axis and a lens radius;
   an optical fiber having a longitudinal axis and having an output surface positioned proximal to the lens, the output surface having an output surface diameter that is less than or equal to the lens radius; and
   wherein the output surface is eccentric to the principal axis; further comprising
   a lateral delivery cap that includes the optical redirection element and has a longitudinal centerline;
   wherein the optical fiber is within the lateral delivery cap, and the longitudinal axis of the optical fiber is not parallel to the lateral delivery cap longitudinal centerline.

2. An optical device for orthogonal redirection of electromagnetic radiation, comprising:
   an optical redirection element that includes a lens and an total-internal-reflectance (TIR) bevel, the lens having a principal axis and a lens radius;
   an optical fiber having a longitudinal axis and having an output surface positioned proximal to the lens, the output surface having an output surface diameter that is less than or equal to the lens radius; and
   wherein the output surface is eccentric to the principal axis;
   the optical device further comprising:
   a lateral delivery cap that includes the optical redirection element and has a longitudinal centerline; and
   wherein the optical fiber is within the lateral delivery cap, and the longitudinal axis of the optical fiber is parallel to but not centrosymmetric with the lateral delivery cap longitudinal centerline.

3. The optical device of claim 2, wherein the output surface is external to the principal axis.

4. The optical device of claim 2, wherein the longitudinal axis of the optical fiber is parallel to the principal axis.

5. The optical device of claim 2, wherein the lens is a convex lens.

6. The optical device of claim 5, wherein the output surface is either perpendicular to the longitudinal axis of the optical fiber or planar and angled relative to the longitudinal axis of the optical fiber.

7. The optical device of claim 2, wherein the lens is a conical lens.

8. The optical device of claim 7, wherein the output surface is either perpendicular to the longitudinal axis of the optical fiber or planar and angled relative to the longitudinal axis of the optical fiber.

9. The optical device of claim 2 further comprising a central-output ray angle that is greater than about 80 degrees.

10. The side fire optical device of claim 2, wherein the longitudinal axis is offset from the lateral delivery cap longitudinal centerline by about 0.5 to about 1.5 times a cross-sectional radius of the optical fiber.

11. The side fire optical device of claim 2, wherein the optical fiber includes an output face that is perpendicular to the fiber axis.

12. The side fire optical device of claim 2, wherein the optical fiber includes an elliptical output face; wherein the elliptical output face is at an angle α to the fiber axis, wherein α is less than 89°.

13. The side fire optical device of claim 2, wherein the lens is centrosymmetric about the lateral delivery cap longitudinal centerline.

14. The side fire optical device of claim 13, wherein the lens is convex.

15. The side fire optical device of claim 13, wherein the lens is conical.

16. The side fire optical device of claim 15, wherein the optical fiber includes an elliptical output face; wherein the elliptical output face is at an angle α to the fiber axis, wherein α is less than 89°.

17. The side fire optical device of claim 2, wherein the lateral delivery cap is adapted to provide a central ray output of greater than 85°.

18. The side fire optical device of claim 2, wherein the lateral delivery cap is adapted to provide a beam divergence maximum of less than 12° half angle in 5% saline.

19. An optical device for orthogonal redirection of electromagnetic radiation, comprising:

an optical redirection element that includes a lens and an total-internal-reflectance (TIR) bevel, the lens having a principal axis and a lens radius;

an optical fiber having a longitudinal axis and having an output surface positioned proximal to the lens, the output surface having an output surface diameter that is less than or equal to the lens radius; and wherein the output surface is eccentric to the principal axis;

the optical device further comprising:

a tube portion having a one-piece construction consisting of fused quartz and/or fused silica, including a guide section and an open-end section, the open-end section and the guide section divided by the lens, the open-end section including a bore which terminates at the lens, the open-end section shaped to receive the optical fiber, the guide section including a light path from the lens to the TIR bevel and then to a transmitting surface, the TIR bevel configured to direct electromagnetic radiation from the lens through the transmitting surface at a side of the tube portion;

and wherein the optical fiber is asymmetrically positioned within the bore of the open-end section.

* * * * *